(12) United States Patent
Liu

(10) Patent No.: US 6,475,531 B1
(45) Date of Patent: Nov. 5, 2002

(54) SAFE BOTANICAL DRUG FOR TREATMENT AND PREVENTION OF INFLUENZA AND INCREASING IMMUNE FUNCTION

(76) Inventor: Yaguang Liu, 67-08 168th St., Flushing, NY (US) 11365

( * ) Notice: Subject to any disclaimer, the term of this patent is extended or adjusted under 35 U.S.C. 154(b) by 0 days.

(21) Appl. No.: 09/795,012

(22) Filed: Feb. 28, 2001

(51) Int. Cl.⁷ ............................................... A61K 35/78
(52) U.S. Cl. ...................................................... 424/725
(58) Field of Search ......................................... 424/725

(56) References Cited

U.S. PATENT DOCUMENTS

| | | | |
|---|---|---|---|
| 4,886,666 A | * 12/1989 | Liu | 424/725 |
| 4,944,945 A | * 7/1990 | Liu | 424/725 |
| 4,944,946 A | * 7/1990 | Liu | 424/725 |
| 4,985,247 A | * 1/1991 | Liu | 424/725 |

FOREIGN PATENT DOCUMENTS

JP 11060599 * 3/1999

* cited by examiner

*Primary Examiner*—Jean C. Witz

(57) ABSTRACT

This invention relates to new safe botanical drug, which is used for treatment and prevention of influenza and increasing immune function. Specifically, this invention provides a method for producing pure Banlangensu (PBLG), BLG's Polysaccharide and Isatin B.

6 Claims, No Drawings

SAFE BOTANICAL DRUG FOR TREATMENT AND PREVENTION OF INFLUENZA AND INCREASING IMMUNE FUNCTION

BACKGROUND OF THE INVENTION

The present invention related to novel pharmaceutical composition for treatment and prevention of influenza caused by viruses and increase immune function, processed for the production of these pharmaceutical compositions and the use thereof The bifunctional pharmaceutical composition is nontoxic.

Specifically, this invention provides a new safe pharmaceutical composition of pure Banlangensu, which is extracted from among *Isatis tinctoria* L, I. *Indigotica Fort* or *Baphicacanthus cusia* Bremek.

DESCRIPTION OF THE PRIOR ART

The major antiviral drugs can inhibit viral replication but also inhibit some host cell function and possess serious toxicity. For example, amantadine, idoxuridine, cytarabine, vidarabine are major antiviral drugs using in clinic now. Amantadine can inhibit myxoviruses, e.g., influenza A, rubella. The most marked toxic effects of amantadine are central nervous system sign, insomnia, slurred speech, dizziness and ataxia. Idoxuridine can inhibit the replication of herpes simplex virus n the cornea, however DNA synthesis of host cells is also inhibited. Cytarabine can inhibit DNA synthesis and interferes with replication of DNA viruses. But cytarabine also inhibits immune function in human. By weight it is about 10 times more effective than idoxuridine, and it is also 10 times more toxic for host cell. Vidarabine can inhibit herpesvirus, but it is also produce more marked adverse gastrointestinal or neurological side effects.

DETAILED DESCRIPTION

Influenza (flu) is a serious of illnesses and it kills more than 20 million of people worldwide in history. The proportion of deaths attributed to influenza reported by 122 cities exceeded the epidemic threshold for 22 consecutive weeks, beginning the week ending Nov. 27, 1999, through the week ending Apr. 22, 2000 in the U.S. Influenza is responsible for approximately 20,000 deaths and 110,000 hospitalizations annually in the U.S.

The most effective way to reduce the impact of influenza is to vaccinate people at high risk for complications shortly before the influenza season each year. But influenza viruses have many different strains.

Vaccine production takes six months, so timely recognition of emerging variants is a key to preventing influenza pandemic. However, after madding vaccine, the new influenza virus strain may be produced again.

Influenza viruses are classified as types A, B, and C. The forms are further identified on the basis of a protein called hemagglutinin, which protrudes from the viral surface. It is the main target for vaccine design because of its role in attaching the virus to cell receptors and inducing neutralizing antibodies. Influenza viruses have many viral surfaces. It causes very difficult to make vaccine on time for prevention of influenza viruses.

As mentioned above, all anti-flu drugs have more side effects. According to FDA report (Nov. 6, 2000), more serious problems are that several anti-flu drugs, which contained phenylpropanolamine (PPA), will cause stroke. Patients, who used drug contained PPA, have 1600% (sixteen times) incidence of stroke than normal people. Therefore, some anti-flu drugs have very high side effects.

Viruses are obligate intracellular parasites. Their replication depends on metabolic processes of the host cell. Therefore, major antiviral drugs that inhibit viral replication also inhibit some host cell functions and possess serious toxicity.

The common cold, for example, is caused by a great variety of different viruses. That is why the same person may have so many different attacks, and why the symptoms may be a bit different from one attack to another.

So much more, the immune function normally protects human being from infections caused by viruses. The results of research indicated that viral infection tends to cause disease only in individual whose immune function has been severely weakened. Individual with health immune function could control virus without the serious effects that occur with the disease. For reasons given above, a new pharmaceutical composition, which has bifunction-inhibiting viruses and increasing immune function, is very important for treatment and prevention of influenza viruses caused by virus. Pure Banlangensu (PBLG) just has above bifunction.

In short, PBLG can inhibit viruses and increase immune function and it is safety.

The following specific examples will provide detailed illustrations of methods of producing PBLG according to the present invention and pharmaceutical dosage units containing PBLG. Moreover, examples will be given of pharmaceutical testing performed with PBLG, which demonstrates its effectiveness in inhibiting viruses and increasing immune function. These examples are not intended, however, to limit or restrict the scope of the invention in any way, and should not be construed as providing conditions, parameters, reagents, or starting materials which must be utilized exclusively in order to practice the present invention.

EXAMPLE 1

Ingredients of PBLG

1. The PBLG Comprises Two Ingredients: Isatin B and BLG's Polysaccharide

Chemical structures of ingredients are shown as below.

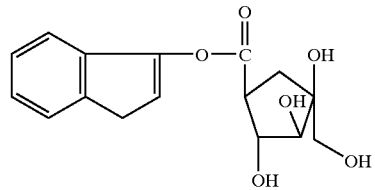

Fig. 1 Structure of Isatin B

-[→4)-α-D-Glu-(1-4)-α-D-Glu-(1[→)-α-D-Glu-(1-]₇-4)-α-D-glu-(1-]r

6

↓

1

α-D-Glu

Fig. 2 Probable structural units of BLG's Polysaccharide

2. Chemical and Physical Information
   A. Isatin B
   a. Molecular formula: $C_{13}H_9O_7$
   b. Molecular weight: 277
   c. Physical data:
      Properties: needles
      mp 326° C.,
      $Uv\lambda_{max}^{Meoh} cm^{-1}$: 246, 272, 302, 480.

IR$\lambda_{max}^{KBr}$cm$^{-1}$: 3240 (NH$_2$), 1674 (C$_3$—CO), 1610 (C$_2$—CO), 1240 (C=C).

B. BLG's Polysaccharide

Molecular weight: about 50.000

$[\alpha]_D^{22}$:+14.0° C.

Ir$\lambda$.cm$^{-1}$ 840

EXAMPLE 2

Percentage of Ingredients (1) The weight percentage in PBLG is that preferred composition in weight percentage of Isatin B is 30~70% and BLG's Polysaccharide is 30~70%. The preferred percentage indicated that BLG's polysaccharide is 70% and Isatin B is 30%.

(2) Clinical use:

The standard dose of PBLG is 100 mg orally daily.

EXAMPLE 3

Manufacture Process

Isolation of BLG's Polysaccharides 10 kg of dried powder of plant was extracted with hot water 20 liters. The extract was filter. Filtrate was dialyzed against running water through cellulose, and the residual solution was concentrated to a small volume. Added ethanol to residual solution and then gave a precipitate (1) that was collected by centrifugation. Precipitate (1) was extracted with aqueous 0.4% sodium borate, and the residue was collected by centrifugation, suspended in water, acidified weakly with acetic acid, dialyzed against running water, and lyophilized to give fraction 1. The fraction A was treated ethanol and precipitate (2) was collected by centrifugation. Precipitate (2) dissolved in water was applied to column of sepharose 2B. Elution with water gave fraction A and then fraction B. Fraction A and B precipitated by ethanol and gave precipitate (3) and collected by centrifugation. Precipitate (3) was dried by washing with acetone and then ether and dried in vacuum. The dried powder is BLG's Polysaccharide.

Isolation of Isatin B 10 kg of dried powder of plant was extracted with hot water 20 liters. The extract was filter. The filtercake extracted with methanol (10 liter). Methanol was recovered under reduced pressure and residue obtained. The residue was extracted with chloroform (5 liter). The chloroform residue was then chromatographed on silica gel G (1 kg), using chloroform as developing solvent. The eluate was concentrated and rechromatographed on silica gel G (500 g) with chloroform as solvent. The active substrace was crystallized from a mixture of chloroform and recrystallized and then dried under vacuum.

EXAMPLE 4

Extraction of Banlangensu (BLG)

The roots of *Isatis tiatis tinctoria* L, or *I. indigotica* Ford were dried and powdered. 3 liters of 95% ethanol was added to 1 kg powders of roots and allowed to stand for one day at room temperature. The solution was filtered and the extract filtrate saved. 2,000 ml of ethanol was added to the residue and refluxed in a water bath for 6 hours. The refluxing was repeated twice by collecting the ethanol, replacing it with an equal volume of fresh 95% ethanol and refluxing for 6 hours. The refluxed ethanol was cooled and filtered and the filtrate combined with the extract filtrate. Ethanol was then recovered by reduced pressure distillation and the residue dissolved in 500 ml of distilled water. The lipid component was removed with 5 changes of ether by adding 500 ml to the water phase for each extraction. An equal volume of water-saturated butanol was added to the final water phase and the butanol was then distilled under reduced pressure. The residue powder was dissolved in 500 ml of ethanol and 2,000 ml of acetone was added to the ethanol with constant stirring while a precipitate formed. The precipitate was washed twice each with acetone and ether and dried.

EXAMPLE 5

Manufacture of PBLG Oral Preparation 4 kg isatin B mixed with 1 kg lecithin as mixture (1). The mixture (1) was mixed with 6 kg of BLG's Polysaccharide as mixture (2). The mixture granulated accorded to the conventional wet granulation method. The mixture content decreased from 100% to 93%. The 7% of content was different types of fillers. Disintegrants, lubricants and glidants were used: microcrystalline cellulose (avicel PH 105, PH 101, PH 102, PH 200, all from FMC Corp., Lehmann and Voss and Co., Hamburg, Germany; and Vivacel 200, Rettenmaier and Söhne GmbH, Ellwangen-Holzmühle, Germany), microfine cellulose (Elcema P 050, P 100, G 250, all from Degussa AG, Frandfurt, Germany; and Tablettierhilfsmittel K, Merck KGaA, Darmstadt, Germany), lactose cellulose granulate (Cellactose, Meggle, Wasserburg, Germany), a-lactose monohydrate (Lactose D 80, Meggle, Wasserburg, Germany), and modified maize starch (Starch 1500, Colorcon GmbH, Königstein, Germany).

The disintegrants tested were the following: cross-linked sodium carboxymethylcellulose (Ac-Di-Sol, FMC Corp./lehmann and Voss and Co.; and Nymcel ZSB 10, Nymcel ZSB 16, METSÄ-SERLA, Njimegen, Netherlands), Cross-linked calcium carboxymethyl-cellulose (ECG 505, FMC Corp./Lehmann and Voss and Co.), potato starch (Caeleo, Hilden, Germany), sodium starch glycolate (Explotab, Gustav Parmentier, Frankfurt, Germany; and Primojel, AVEBE Deutschland, Düsseldorf, Germany), cross-linked polyvinylpyrrolidone (Kollidon CL, BASF AG, Ludwigsburg, Germany; and Polyplasdone XL, ISP Deutschland, Frechen, Germany), and low-substituted hydroxypropyl-cellulose (L-HPC LH 22, L-HPC LH 31, both from Shin-Etxu Chemical Co., Ltd., Tokyo, Japan).

For lubrication, the following were used: magnesium stearate (Otto Bärlocher GmbH, Munich, Germany), glyceryl tristearate (Dynasan 118, Hüls Ag, Witten, Germany), and polyethylene glycol (PEG 6000, Hoechst AG Frankfurt/Main, Germany).

As glidants, colloidal silicon dioxide (Cab-O-Sil M 5, Cabot GmbH, Hanau, Germany; Syloid 244, W. R. Grace and Co., Lexington, Ky., and Aerosil 200, Degussa AG, Frankfurt/Main, Germany) and hydrophobic colloidal silicon dioxide (Aerosil R 972, Degussa AG) were used. As a stabilizer, ascorbic acid (Merck KGaA, Darmstadt, Germany) was added.

The content of oral PBLG was kept constant at a level of 100 mg per tablet. Tablet weight was varied between 100–105 mg. Tablet mixtures were mixed for 10 min in the Turbula mixer (type T2C, Willy Bachofen, Basel, Switzerland). The n lubricants were sieved through a 315-μm sieve into the mix. Final mixing was carried out for 5 min at 42 rpm in the Turbula mixer. The mixtures were compressed using a rotary press (Korsch PH 103, Korsch, Berlin). The lower compression roller was instrumented with four strain gauges (type 3/120 LY 11, Holtinger Baldwin, Inc., Darmstadt, Germany). A Philips carrier-frequency bridge (PR 9307 Philips, Kassel, Germany) was used for signal amplification. Each batch was compressed at different levels of compression force in the range of 1 to 25 kN. As a stabilizer, ascorbic acid (Merk KGaA, Darmstadt, Germany) was added. Sugar-coating operation was also performed conventionally.

EXAMPLE 6

Storage Condition for the Drug Product

The packed oral PBLG preparation was sealed, protected from lightness, and stored in cold area. Storage condition: <20° C., moisture 65–70%.

EXAMPLE 7

Determination of PBLG
A. Determination of BLG Polysaccharide

Electrophoresis. Glass-fiber paper-electrophoresis was conducted on What-man GF-81 glass-fiber paper (4×40 cm) with 0.1 M sodium hydroxide containing 0.05 M sodium tetraborate for 1.5 h at 250V. The spot was detected with the 1-naphthol-sulfuric acid reagent. G-A gave one spot at a distance of 9.5 cm from the origin.

Gel filtration. The sample (2 mg) was dissolved in 0.3 M sodium hydroxide (0.5ml), and -applied to a column (1.5×96 cm) of Sepharose CL-4B. The column was eluted with 0.3M sodium hydroxide at a flow rate of 6 ml/h. Fractions (4 ml each) were collected, and an aliquot of each fraction was analyzed by the phenol-sulfuric acid method.
B. Determination of Isatin B
  a. Method: HPL
     Apparatus: HPLC (TOYO SODA-CCPW);
     Ultraviolet detector (TOYO SODA-SF 770);
     Condition: ODS column (4 mm×25cm); acetonitrile-water (53:47) as mobile phase; detection wave length 208 nm; flow rate 1.0 ml/min.
  b. Standard curve: Precisely weighed proper amount of standard Isatin B, dissolved in methanol, fixed to 2 mg/ml as standard solution. Internal standard was fixed to 10 μl/ml by dissolving dimethylbenzene and methanol. Accurately took out 0.25, 0.15, 0.10 and 0.05 μl of standard solution, to standard solution added with internal standard 2 μl respectively, and added methanol to 1 ml. Standard curve was made. The results demonstrated that the liner relation was occurred between peak area and concentration of the Isatin B. The regression index was $Y=9.651\times10^{-4}+0.045$, $r=0.968$.
  C. Sample detection: Powder of sample 0.5 mg placed into 5 ml flask. 5 ml of methanol was added to flask, mixture extracted by ultrosonic vibration for 20 min. The sample solution was detected and compared with standard curve. To calculated the content of Isatin B in each sample.

EXAMPLE 8

Quality of the Product a. The reports of manufacturing factory were described the quality examinations each batch, including appearance and chromatogram analysis.

b. Validity of the product out of factory: 1.5 year.

c. Stability: Each parameter of the product after 3 years of observation when stored in normal condition.

EXAMPLE 9

Inhibition of Influenza Virus in Mice by PBLG

Influenza viruses cause respiratory tract in infections in a wide range of species including mice and ferrets. In fact, mice and ferrets have been frequently used as models for research of influenza virus infection in human. We now report that PBLG protects mice and ferrets against the effects of influenza virus infection.

Virus: Influenza virus strain influenza A/Beijing/32/92 ($H_3N_2$) was grown in the allantoic cavity of 10-day old embryonated eggs for 40–48 hours. The infectious allantoic fluid was stored at −70° C. until use. Virus titers were expressed as hemagglutinin units (HAU) or as median egg infectious doses ($EID_{50}$). The virus was purified as described by Laver and was inactivated under ultraviolet light (UV).

Animal: Male white Swiss mice weighing about 22–24 g were used in experiments.

Influenza virus infected in mice. Mice were anesthetized by inhalation of ether and were inoculated intranasally with 400 μl of virus suspension (approximately) 20 μl into each nostril. Each mouse received $1.0\times10^{30}$ 50% tissue culture infective doses (TCI $D_{50}S$) of influenza A/Beijing/32/92 (H3N2), which was nonlethal challenge.

Treatment procedure. A single dose of PBLG was administered by oral at time 3 h prior to virus infection. Control animals received distilled water only. Dose of PBLS was 100 mg/kg. The virus tilter in lung homogenates were used for efficacy tests, the period of observation was over the 7 days post infection. Also, reduction in lung consolidation and reduction in mortality were observed. In designated day ten animals from each group were killed, the lung was removed aseptically, and the extent of consolidation was expressed as a percentage of the total lung surface. The titer of influenza infections virus in lung homogenate was determined by enzyme-linked immunosorbent assay by method described previously or the titers of influenza virus were determined by a plaque assay as described preciously. The methods for deriving the percent area under the virus titer days curve (AUC) for virus titers in lung homogenated of mice and methods were as described previously.

The data of efficacy of PBLG in treated mice ever a 7-day period (in groups of five mice each). In term of reduction in mortality, virus titers in lung homogenates, and lung consolidation scores summarized in Table 1.

TABLE 1

Efficacy of PBLG on influenza A/Beijing/32/92 (H$_3$N$_2$)

| Group | No. of samples | Group median virus titers in lung homogenate (log$^{10}$ TCID$_{50}$S/ml) on days | | | | | | No. of mice dead/ total no. of mice | % AUC |
|---|---|---|---|---|---|---|---|---|---|
| | | 1 | 2 | 3 | 4 | 5 | 6  7[a] | | |
| PBLG | 20 | 3.0 | 3.5 | 4.0 | 5.0 | 4.8 | 3.8  3.6 | 4/50[b] | 25 |
| Control | 20 | 5.0 | 6.3 | 7.5 | 6.8 | 6.6 | 5.7  0* | 50/50 | 100 |

[a]Unschedule death;
[b]P < 0.01;
*No survivors

The data of Table 1 showed that PBLG significantly reduced mortality over the 7-day period virus titers were reduced in lung homogenates on day 2 and day 3.

EXAMPLE 10

Effect of PBLG on Virus Plaque Inhibition Assay

Cell culture. Madin-Darby canine kidney (MDCK) cells were passaged weekly with growth medium consisting of Eagle minimal essential medium, glutamine, 10% heat-inactivated fetal bovine serum, penicillin, and gentamicin.

For PBLG susceptibility testing (below), disposable 35-mm plastic culture dishes were seeded with approximately 10$^5$ MDCK cells in 2.0 ml of growth medium and incubated with 5% CO$_2$ at 36° C. for 3 to 5 days, until confluent monolayers had grown.

Viruses. Four strains of influenza A viruses, and one of influenza B viruses were used in theses studies. The influenza A viruses was A/Beijing/32/92 (H$_3$N$_2$), A/Singapore/1/75 (H2N2), A/England/939/69 and A/Brazi/11/78 (H1N1); the influenza B viruses were B/Hong Kong/76.

Virus stocks were prepared in embryonated eggs (1 to 14 passages), and samples of allantoic fluid were stored at −70° C. For susceptibility tests, virus dilutions were made in Hanks balanced salt solution (pH 7.2 to 7.4) containing 0.5% gelatin.

Plaque inhibition assay. PBLG susceptibility tests were performed with modifications of methods described by Kremzner and Harter and by Tobita et al. Triplicate monolayers of MNCK cells in 35-mm culture dishes were washed free to protein-containing growth medium before use and preincubated with 0.2 ml of doubly concentrated Eagle minimal essential medium (pH 7.2 to 7.4) containing 4 μg/ml trypsin and the test PBLG in double concentration (50 and 100 μg/ml). An equal volume of virus suspension, containing 50 to 150 plaque-forming units, was added 5 to 10 min later, and plates were incubated at 36° C. for 60 min with frequent shaking. A 0.6% agarose overlay (3 ml) containing Eagle minimal essential medium, trypsin (2 μg/ml), and the appropriate PBLG dilution was added to each plate. Plates were incubated at 36° C. in a humidified atmosphere of 5% CO$_2$ in air. After 36 to 48 h, plaques were stained with neutral red and counted. The final concentration of PBLG is 100 μg/ml. The 50% of inhibitory concentration (IC$_{50}$) was calculated. The results of PBLG on influenza viruses are summarized in Table 2.

TABLE 2

Comparative activity of PBLG drug in a plaque inhibition assay

| | IC50 (100 μg/ml) [a] | | |
|---|---|---|---|
| Virus strain | PBLG | Amantadine | Ribavirin |
| A/Beijing/32/92 (H3N2) | 36 | 25 | 90 |
| B/Hong Kong/76 | 61 | 125 | 54 |
| A/Singapore/1/75 (H2N2) | 32 | 11 | 82 |
| A/England/939/69 | 30 | 21 | 46 |
| A/Brazil/11/78 (H1N1) | 40 | 38 | 56 |

[a] Results are expressed as the results of individual assays or as mean ± standard deviation when multiple assays were performed.

Data of Table 2 showed that PBLG could significantly inhibit various influenza viruses including A/Beijing/32/92 (H3N2), B/Hong Kong/76, A/Singapore/1/75 (H2N2), A/England/939/69, and A/Brail/11/78 (H1N1).

Data of Table 2 also showed that PBLG is compared directly with amantadine and ribavirin against influenza A and B in mice by oral route of administration. The efficacy of PBLG is between amantadine and ribavirin.

EXAMPLE 11

Effect of PBLG on Inhibition Influenza Virus of Chick Embryo Cell System

PBLG inhibits the multiplication of influenza virus in eggs and mice. The present investigation has attempted to determine PBLG inhibited influenza by plaque of virus-chick embryo cell system. Cell cultures. Chick embryo cells, prepared from 11-day-old embryos by trypsinization, were seeded into 60-mm plastic petri dishes. When used after overnight incubation, the cultures contained approximately 4×10$^6$ cells per dish. Eagle's minimum essential medium (MEM) without serum was used as maintenance medium for the cultures. Infectivity titrations were performed in monolayer cultures of chick embryo cells.

Hemonagglutination titrations. 0.2 ml of serial 2-fold dilutions of virus in phosphate-buffered saline (PBS) was added to 0.2 ml of a 1% suspension of chicken red blood cells in PBS. Replicate cultures of chick embryo cell monolayers in petri dishes were washed with PBS, and 2 ml of Eagle's MEM with or without PBLG (100 μg/ml) was added to each culture. After incubation for 1 hour at 37° C., the medium was removed, and the cultures were incubated with 0.5 ml of virus with or without PBLG for 30 min at 37° C. Then, the cultures were washed twice with PBS with or without PBLG 2 ml of Eagle's MEM with or without PBLG was added, and the dishes were incubated at 37° C. in a 5%

$CO_2$ atmosphere. In one type of experiment, PBLG (0.1 ml) was added to the cultures 1.5 hours after virus inoculation. The final concentration of PBLG was 100 μg/ml. Control cultures received 0.1 ml of PBS. At intervals after virus inoculation, two dishes were frozen at −35° C. subsequently, they were thawed, the cell sheets were scraped off the plastic surface, and cells with their medium were harvested. Samples were rapidly frozen and thawed three times and centrifuged at 300rpm for 10 min to remove debris. The supematants were stored at −35° C. until assayed. Thus, the total amount of virus produced was measured. The time of virus inoculation was considered zero time.

Infective center assay. Monolayers of chick embryo cells to be assayed were washed once with PBS deficient in calcium and magnesium, and 1 ml of warm 0.25% trypsin was added to the cultures. After incubation at 37° C. for 1 min, the trypsin was removed. After additional 3 minutes incubation at 37° C., the cells were suspended in Lavit medium with 5% heat-inactivated calf serum. Serial 2-fold dilutions of the suspended cells were made with Lavit medium, and 0.2 ml of each dilution was inoculated into monolayer cultures of chick embryo cells. At least three dishes were used per dilution. The suspended cells were immediately distributed in 1 ml of agar overlay followed by an additional 2 ml of agar overlay 20 min later. All dishes were incubated for 2 days at 37° C. in a 5% $CO_2$ atmosphere prior to staining with neutral red.

Preparation of neutral red-labeled virus. Monolayer cultures of chick embryo cells were grown for 1 day in the usual growth medium which was then replaced with Eagle's MEM containing neutral red (10 μg/ml). After an additional 24 hours' incubation, the cultures were infected with virus, Eagle's MEM containing neutral red was added, and the cultures were incubated overnight at 37° C. in a 5% $CO_2$ atmosphere. Then, the medium was harvested. Virus was passaged in the presence of neutral red 4 or 5 times. All operations involving neutral red-labeled virus were conducted under red light which had been shown to be noninactivating.

Photodynamic inactivation of neutral red-labeled virus. One milliliter of virus material diluted 1:10 in PBS and placed in a 60-mm plastic petri dish, or infected monolayer cultures covered with 1 ml of PBS, were expected for 15 min at room temperature to a 100-W white lamp at a distance of 3.5 cm. Between the lamp and the petri dish a large glass dish filled with water was placed to absorb radiant heat. The surrounding atmosphere was cooled by fans during irradiation. The hemagglutination inhibition titer of the serum was 640 against 4 hemagglutinin units of virus. At a concentration of 25 μg/ml, PBLG causes no visible inhibition virus. But at 50 μg/ml inhibition of virus was observed and at 100 μg/ml, PBLG had a significant antiviral effect. The data are summarized in Table 3.

TABLE 3

Antiviral activity of PBLG by viral plaque

| Concentration of PBLG (μg/ml) | Plaque per plate |
|---|---|
| 0 (control) | 51 ± 6 |
| 10 | 45 ± 5 |
| 25 | 44 ± 5 |
| 50 | 40 ± 6 |
| 75 | 26 ± 4** |
| 100 | 9 ± 1* |

The cultures were infected with 50 PFU virus,
*Significant different from control group; $P < 0.001$.
**Significant different from control group; $P < 0.01$.

EXAMPLE 12

Effect of PBLG on Nasal Virus Titers in Ferrets Infected with in Influenza A Virus Adult female ferrets (1.0–1.4 kg average weight 1.2 kg) were used while under light anesthesia groups of five ferrets were infected by intranasal instillation of 250 μl of influenza virus B/Hong Kong/5/72 containing 105 $TCID_{50}$/m.

Dose of PBLG was administered by oral at 100 mg/kg. Other methods are same as described previously.

Effect of PBLG on nasal virus in ferrets infected is summarized in Table 4–5.

TABLE 4

Efficacy of PBLG on ferrets infected with influenza (1)

| Treatment | No. of animals | % Reduction in mean nasal wash virus titer | | | |
|---|---|---|---|---|---|
| | | 1 | 2 | 3 | Average of 1–8 |
| Control | 8 | 0 | 0 | 0 | 0 |
| PBLG | 8 | 98.5* | 96.7* | 80.5* | 62.0** |

* Significant different from control group, $P < 0.001$
** Significant different from control group, $P < 0.01$

TABLE 5

Efficacy of PBLG on ferrets infected with influenza (2)

| | Nasal wash virus titer (log$_{10}$ $TCID_{50}$ s/ml)[a] | |
|---|---|---|
| Time (h) post infection | Untreated (control) | PBLG (100 mg/kg) |
| 12 | 0.30 ± 0.40 | 0.11 ± 0.55** |
| 24 | 0.32 ± 0.55 | 0.01 ± 0.00* |
| 30[b] | 4.80 ± 0.50 | 2.90 ± 0.40** |
| 36 | 4.20 ± 0.58 | 2.95 ± .045** |
| 48 | 3.50 ± 0.45 | 3.40 ± 0.50 |
| 54 | 2.50 ± 0.40 | 2.45 ± 0.40 |
| 60 | 3.50 ± 0.55 | 2.20 ± 0.30 |
| 72 | 3.00 ± 0.50 | 2.00 ± 0.35 |
| 90 | 2.05 ± 0.35 | 1.25 ± 0.20 |

[a]Data represent the mean ± Standard deviations for duplicate measurements with the nasal wash samples obtained from animals.
[b]Peak virus titers were detected at 30 h post infection.
*Significant different from control group; <0.001.
**Significant different from control group; <0.01.

As data of Table 4 indicated that nasal wash virus titers reduced by 98.5, 96.7, and 80.5 at day 1, day 2, and day 3, respectively. Data of Table 5 indicated that PBLG could significantly inhibited virus. In nasal wash, when 24 post infection, PBLG almost completely inhibited virus, the percentage of inhibition was 97% and when 12 post infection, the percentage of inhibition was 64%.

EXAMPLE 13

Effect of PBLG on Influenza Virus Titer

Individual lung homogenates prepared from mice were described preciously. The titers of lung virus were assayed by enzyme-linked immunosorbent assay (ELISA). Reduction in virus titer was expressed as percentage of values from control animals.

The data of inhibiting virus by PBLG are summarized in Table 6.

TABLE 6

Effect of PBLG on virus titer reduction

| Time of prophylatic dose relative to time of infection (h) | Mean lung virus titers $(\log_{10} TCID_{50}) \pm SD$ in animals | | No. of virus-fee animals/No. of animals in treatment group (%) |
|---|---|---|---|
| | PBLG | Control | |
| −3 | 2.90 ± 0.35* | 7.00 ± 0.65 | 71.5 |
| −12 | 4.15 ± 0.50* | 7.00 ± 0.70 | 40.0 |
| −36 | 4.30 ± 0.48** | 7.00 ± 0.65 | 38.5 |
| −48 | 4.50 ± 0.55** | 6.80 ± 0.70 | 35.0 |
| −72 | 4.80 ± 0.50** | 7.00 ± 0.75 | 33.3 |
| −120 | 5.10 ± 0.65 | 7.45 ± 0.70 | 22.8 |
| −180 | 5.50 ± 0.60 | 7.50 ± 0.80 | 20.5 |
| −240 | 5.55 ± 0.55 | 5.80 ± .065 | 15.6 |

*Significant different from control groups; P < 0.01.
**Significant different from control groups; P < 0.05.

Data of Table 6 indicated that PBLG could significantly inhibit influenza virus at between −3 h to −36 h, and also showed both in vitro and in vivo models of mice to be effective antiviral agent for influenza. PBLG Significantly increased in number of virus-fee animals in treatment group. Treatment at −3 h, virus-fee animals reached to 71.5% and if treatment at −240 h, % virus-fee animal was 15.6% only.

EXAMPLE 14

Effect of PBLG on Survivors of Eggs

The preparation of chick embryo fibroblast cultures, their use in the disc-plate plaque-suppression test, and the infection and treatment of embryonated eggs had been described.

TABLE 7

Antiviral activity of PBLG against influenza virus

Survivors/total eggs

| PBLG (20)* | Control (20) | Normal (20)*** |
|---|---|---|
| 14/20 (70%)** | 0/20 (0%) | 20/20 (100%) |

Eggs incubated at 36° C. for 10 days and eggs were treated 24 h prior to addition of virus
*Number is parentheses indicated numbers of samples.
**P < 0.001 compared to control eggs in the experiment
***No virus, no drug.

The data summarized in Table 7. PBLG was investigated and found to have an anti-influenza virus effect in eggs and cell culture. The percentages of survivors are 100%, 0, and 70% for normal group (no drug, no virus), control group (no drug+virus) and PBLG group (PBLG+virus), respectively.

EXAMPLE 15

The Effect of PBLG on Virus in Chick Embryo

For determination of inhibition of drug injection on flu virus in chick embryo, 0.2 ml 30 $EID_{50}$ flu virus inflected in chick embryo allantoic cavity, 0.5 ml drug injection and bouillon (as control) were injected through same inoculation pathway in different time. Chick embryo allantoic fluid Blood coagulation geometric average value was determined after infected and incubated 48 h. The results were shown in Table 8.

TABLE 8

Inhibition of PBLG in influenza virus in chick embryo

| | Virus blood coagulation geometric average value | | | |
|---|---|---|---|---|
| | A/Beijing/32/92/(H3N2) | | B/Hong Kong/76 | |
| Group | PBLG | Control | PBLG | Control |
| Before infected 30 min | 30** | 402 | 18** | 380* |
| Before infected 2 h | 205** | 1800 | 12** | 510 |
| Before infected 4 h | 328* | 956 | 28** | 950 |
| Before infected 24 h | 405 | 1250 | 285* | 1020 |
| After infected 2 h | 910 | 1450 | 892 | 1820 |
| After infected 4 h | 280** | 1680 | 78* | 1205 |
| After infected 24 h | 1280 | 1560 | 990 | 1350 |

*Significant different from control group, P < 0.01;
**Significant different from control group, P < 0.001.

The data of Table 8 showed that two strain influenza viruses could be obviously inhibited by PBLG. Influenza virus was obviously inhibited by PBLG before chick embryo was infected 30 min, 2 h, 4 h, and after chick embryo was infected 2 h and 4 h. Blood coagulation geometric average value of PBLG group was reduced by more 10 times than that of control group. Blood coagulation geometric average value of virus was decreased 4 times before 24 h, but inhibition can't be found after 24 h PBLG was given.

Evaluation of anti-influenza drug needs to be treated in man, but this evaluation is difficult because about 8–10 h elapse from the time the influenza virus enters the nose. It has finished its first reproductive cycle. Cold symptoms typically begin about 10 to 12 h after the virus is first produced in the nose. And symptoms generally peak about 30 to 72 h after infection. By the time a cold has obviously symptoms. It may be too late to alter its course. Therefore, animal model used for test anti-influenza drug is more important.

In our model of influenza virus infection, PBLG could significantly decrease mortality of host. Oral administration of PBLG provided protection against the lethal effect of influenza virus. Infected mice treated with 100 mg of PBLG per kg per day significantly increased in survival rate. After administration of PBLG, 8% of the mice died only as compared with 100% died of the control (Table 3). 90% of mice infected with influenza virus died within 3 to 9 days after infection and 100% died after 10 days. PBLG given at protective doses significantly reduced mortality. Data of Table 1 showed that virus titers (treatment/control) is 48% at 2 days, 46% at 3 days, 74% at 4 days, 70% at 5 days and 77% at 6 days. Above data indicated that PBLG reduced virus titers in lung homogenates significantly.

Data of Table 2 showed that PBLG could significantly inhibit various influenza viruses including A/Beijing/32/92 (H3N2), B/Hong Kong/76, A/Singapore/1/75 (H2N2), A/England/939/69, and A/Brail/11/78 (H1N1). The data of Table 2 also showed that antiviral effects of PBLG are better than ribavirin. However, PBLG is much safe than ribavirin and amantadine. $LD_{50}$ of PBLG (oral) is high than 5.0 g/kg. No sign of drug-related toxicity was detected in the animals in the efficacy studies (see Toxicology Section).

Antiviral activity of PBLG in plaque-suppression tests showed that significant differences were found between different concentrations of PBLG. Data of Table 3 showed at 100 μg/ml, PBLG inhibited 82% and at 10 μg/ml inhibited 12%.

The method of plaque inhibition assay used in a lot of antivirus studies. It is provided to be a rapid, reproducible method for antivirus drug susceptibility of influenza viruses in vitro. The plaque assay utilizes a readily available, continuous cell line. This plaque method allows a high efficiency for influenza.

Data of Table 4 and 5 showed that PBLG can be marked reduction in lung homogenate viral titer and enhanced survival in ferrets infected with influenza. For example, nasal wash virus titers reduced by 98.5%, 96.7%, and 80.5% at day 1, day 2, and day 3, respectively.

The ferret model was useful infection animal model because infected ferret developed a self-limited disease with signs similar to those observed clinically in humans, including fever, increased nasal signs, and general lethargy.

Data of Table 5 indicated that PBLG could significantly inhibited virus in nasal wash. When 24 post infection, PBLG almost completely inhibited virus, the percentage of inhibition was 97% and when 12 post infection, the percentage of inhibition was 64%.

Data of Table 6 indicated that PBLG could significantly inhibit influenza virus at between −3 h to −36 h. Data of Table 6 also indicated that PBLG, an inhibitor of influenza virus, has been shown both in vitro and in vivo models of mice to be effective antiviral agent for influenza. Additional, data of Table 6 showed that PBLG, 36 h prior to infection, significantly reduced lung virus titers in infected mice, compared with untreated (control) animals. PBLG Significant increased in number of virus-fee animals in treatment group was also observed. Treatment at −3 h, virus-fee animals reached to 71.5% and if treatment at −240 h, % virus-fee animal was 15.6% only. Data of Table 7 showed that PBLG has a marked anti-influenza virus effect in eggs. The efficacy of PBLG in this model was evaluated on the basis of the survival rate. When 10th day post infection, for PBLG group, survivors % was 70, and for virus infected group (control) survivors % was 0 and for normal (no virus and no drug) group was 100%.

The data of Table 8 showed that two strain influenza viruses could be obviously inhibited by PBLG. Influenza virus was obviously inhibited by PBLG before chick embryo was infected 30 min, 2 h, 4 h, and after chick embryo was infected 2 h and 4 h. Blood coagulation geometric average value of PBLG group was reduced by more 10 times than that of control group. Blood coagulation geometric average value of virus was decreased 4 times before 24 h, but inhibition can't be found after 24 h PBLG was given.

It is important that our research models include:

a. Animals, which are mice and ferret, and egg;

b. In vivo and in vitro methods; and c. Two strain of influenza viruses: influenza A and B, which include five viruses—A/Beijing/32/92 (H3N2), A/Singapore/1/75 (H2N2), A/England/939/69, A/brazil/11/78 (H1N1), and B/Hong Kong/76.

We also determined various concentrations of PBLG, and virus, and various times (before and after infection). The experimental data in various methods gave a similar result.

In conclusion, PBLG appears to be a remarkable inhibitor or influenza virus infections in vivo and vitro.

PBLG is a new select and safe inhibitor of influenza virus with significant antiviral effect and without an evidence of cytotoxicity (see Toxicology Section). The antiviral activity of PBLG, combined with its lack of apparent cytotoxicity in animal models, makes PBLG an excellent candidate for treatment of influenza virus infections in human.

EXAMPLE 16

Effect of PBLG on Natural Killer Cell Activity

Animals

Male white Swiss mice, weight about 22–24 g, were used in experiments. Two groups of mice were administered with oral dose of 100 mg/kg (treatment group) or distilled water (control group) every day for two times. One week after the treatment, mice were sacrificed for in experiments.

Virus

Influenza virus strain A/Beijing32/92/H3N2 was grown in the allantoic cavity of 10-day old embryonated eggs for 40–48 hours. The infectious allantoic fluid was stored at −70° C. until use. Virus titers were expressed as hemagglutinin units (HAU) or as median egg infectious doses ($EID_{50}$). The virus was purified as described by Laver and was inactivated under ultraviolet light (UV).

Cytotoxic T Cell Assay

The generation of cytotoxic T cells to influenza virus had been described previously. Briefly, Swiss mice (22–24 g) in groups of five were given i.v. $10^3$ HAU of influenza virus. Six days later, spleens from each group were pooled and single cell suspensions were made according to blanden and Langman. Cytotoxicity of the splenic lymphocytes was measured as follows: $5\times10^6$ P815 cells in 0.03 ml Eagle's minimum essential medium, which supplemented with 10% hear-inactivated FCS and contained antibiotics, were labeled with 500 $\mu$Ci $^{51}$Cr at 37° C. for 1 hour. After labeling, the cells were washed twice with the culture medium and then divided into two equal lots. One lot was infected with influenza virus (15 $EID_{50}$/cell, 1 h at 37° C.) and the other lot uninfected and used as a control. The target cells were then washed twice and cell concentration adjusted to $1\times10^5$ cells/ml. 0.1 ml was distributed into each well of the 96-well tissue culture trays (Linbro Scientific Co.) and 0.1 ml spleen cell suspensions (effector cells) was added (spleen cells were adjusted to $2.5\times10^6$, and $1\times10^7$ cells/ml so that effector/target cells rations were 25:1, 50:1, and 100:1, respectively). The trays were incubated at 37° C. under a gas phase of 10% $CO_2$ in air for 6 h, after which 0.1 ml of the supernatant from each well was removed and radioactivity counted. For total releasable $^{51}$Cr, 2.0 ml distilled water was added to 0.1 ml target cells and then allowed to stand on the bench for 6 h. This was then spun down and the supernatant was sucked up and radioactivity counted. The percentage specific lysis was calculated as follows:

$$\%\ \text{Specific lysis} = \frac{\text{Test culture counts} - \text{spontaneous release counts}}{\text{Water lysis counts} - \text{spontaneous release counts}} \times 100$$

Natural killer cytotoxicity assay. Mice were treated with PBLG and virus as described before. Two days after the treatment, spleenic effector cells and target cells were prepared. $^{51}$Cr release assay was used and the percentage specific lysis was calculated in the same way as mentioned above.

Measurement of delayed-type hypersensitivity. Delayed-type hypersensitivity (DTH) in mice was determined by measuring footpad swelling. The animals wee first sensitized by injecting subcutaneously $10^3$ HAU infectious virus diluted in 0.3 ml volume of phosplate-buffer saline (pH 7.3) (PBS). Six days later, each mouse was challenged with 30 $\mu$l purified, UV-irradiated virus ($6\times10^3$ HAU), injected into the right hind footpad. The same volume PBS was injected into the left hind footpad as control. It was measured 24, 28 and 72 h after virus challenge with a dial-guage caliper (H. C.

Kroplin, Schluchtern, Hessen, Germany) calibrated to 0.05 mm. Results were calculated as follows:

$$\frac{\text{Mean thickness of right hind footpad} - \text{Mean thickness of left hind footpad}}{\text{Mean thickness of normal footpad}} \times 100$$

Anti-hemagglutinin antibody assay. The serum anti-hemagglutinin antibody titers were determined by the microtitration hemagglutination-inhibition test as described by Braciale and Yap. Briefly, mice in groups of five were bled from the tail veins at different time intervals after immunization with $10^3$ HAU infectious virus (i.v. injection). The blood was allowed to clot at room temperature. The sera were collected and heat inactivated (56° C., 30 min) to remove nonspecific inhibitors. Two-fold serial dilutions of the immune sera were made with PBS in 96-well round bottom tissue culture trays (Llinbro Scientific Co.) in a final volume of 25 μl. four HAU purified virus in a volume of 25 μl was then added to each well. After 30 min incubation at room temperature, 50 μl of 0.5% fowl erythrocytes was added to all wells and the hemagglutination-inhibition endpoints recorded after a further incubation of about 30 min. The titer of the serum was expressed as the reciprocal of the highest dilution of the serum, which still inhibited the hemagglutination.

Statistical analysis. Results are expressed as arithmetic mean±standard error of the mean (S.E.M.). Statistical difference for group comparisons was determined by the Student's "t" test. The data of experiments are summarized in Table 9.

The present study aims at evaluating the effects of administration of PBLG on the immune function of mice infected with influenza virus. The results of Table 9–10 indicated that PBLG significantly increases NK cells and decrease anti-hemagglutinin antibody response to infection of influenza virus.

Example 17

The effect of PBLG on Lymphoblastoid Transformation

A. Methods of Animals are Similar to Previous Section

B. Lymphoblastoid Transformation Test
  1. Reagents and conditions for cell culture:
    a. Culture media—RPMI 1640, medium 199 or minimal essential medium (Eagle).
    b. Buffer—Hepes buffer, the final concentration at 37° C. was 25 mM, to maintain the pH of the medium at 7.31.
    c. Serum—generally 15% fetal bovine serum was incorporated, for lymphocytes from mice, 5% was used.
    d. Gaseous phase—5% $CO_2$ in air.
    e. Cell concentration—generally $1-2 \times 10^6$/ml.
    f. Stimulants—20 μl/ml for phytohemagglutinin containing polysaccharide (PHA-M) or 10 μl/ml for polysaccharide-free purified phytohemagglutinin (PHA-P).

C. Methods of Autoradiographic Counting
  (1) Mixed 1 ml of the venous blood with heparin and incubated at 37° C. for 30 min. Aspirate the leucocyte-rich upper buffy coat layer when the erythrocytes were settled. Added 3 ml of the culture medium to the culture tube and added PHA, and mixed by shaking and sealed tightly with rubber stopper. Incubated at 37° C. for 72 h.
  (2) Added $^3$H-Tdr to 1 μCi/ml and continued the incubation for 2 h.
  (3) Washed the cells with Hanks' BSS for 3 times to get rid of the free isotopes.
  (4) Prepared smears with the washed cells on slides. Air dried and fixed with methanol.
  (5) Diluted the nuclear emulsion with distilled-water to 1:1, soaked the slides in the emulsion, placed them in a light-proof box containing dessicant and exposed for 14 days at 4° C.
  (6) Developed, fixed and stained (method of Sharma).
  (7) Counted 200 cells under the microscope. Nucleus containing more than 10 exposed granules was scored as transformed cell and the transformation rate was calculated.

TABLE 9

Effects of PBLG on NK cell activity of mice

| | % Specific lysis (mean ± SEM) | | | |
|---|---|---|---|---|
| | RBL-5 | | YAC-1 | |
| Treatment | 50:1 | 100:1 | 50:1 | 100:1 |
| Control | 7.8 ± 8.5 | 15.5 ± 1.5 | 40.5 ± 3.6 | 58.2 ± 6.0 |
| PBLG[1] | 10.1 ± 1.2 | 17.8 ± 2.0 | 43.0 ± 3.6 | 60.0 ± 7.1 |
| Virus infected[1] | 30.5 ± 4.0 | 50.0 ± 6.5 | 70.5 ± 7.5 | 80.0 ± 8.5 |
| PBLG and virus infected[2] | 53.5 ± 6.0* | 78.8 ± 8.2* | 91.5 ± 9.5* | 125.5 ± 12.0* |

*Significantly different from virus infected group. $P < 0.001$
[1]Mice were assayed for NK activity in spleens 2 days after administration of PBLG or virus ($10^3$ HAU A influenza virus).
[2]PBLG were administered 2 days before injection of virus and NK activity assayed 2 days after virus infection.

TABLE 10

Effects of PBLG on the anti-hemagglutinin antibody response to influenza virus

| Treatment | Anti-hemagglutinin Antibody titer Day 10 | Antibody titer Day 20 |
|---|---|---|
| Virus infected[1] | 80.5 ± 8.0 (10) | 135.0 ± 14.0 (10) |
| PBLG treated and virus infected[2] | 51.0 ± 6.0* (10) | 85.0 ± 9.0* (10) |

*Significantly different from virus infected group. $P < 0.01$
Number in parentheses is the number of samples in different group.
[1]Mice were injected i.v. with $10^3$ HAU infectious a influenza virus
[2]PBLG was administered to mouse 2 days before virus infection.

D. Measured by Liquid Scintillation (8) The conditions of cell culture were same as above. $^3$H-TdR was added after 48 h of incubation at a final concentration of 1 μCi/ml and continued the incubation for 24 h.

(9) Washed the cells twice with cold normal saline and the erythrocytes were lysed by addition of distilled-water and equal volume of 3.6% NaCl was then added. The intact lymphocytes were again washed once with cold saline. Spun down the lymphocytes and added 2 ml of 10% trichloroacetic acid to precipitate the protein. Washed twice with normal saline. Added 2 ml of ethanol: ether (1:1) to wash once. 0.2 ml of formic acid was then added for digestion till the precipitate was dissolved.

(10) Added 4 ml of scintillation fluid to 0.01 ml of the final sample and counted in a liquid scintillation counter.

The data of experiments are summarized in Table 11.

TABLE 11

| Treatment | n* | C.P.M. |
|---|---|---|
| Virus-infected | 10 | 697 ± 38 |
| PBLG + virus-infected | 10 | 1085 ± 98** |

*Number of samples.
**Significant different from virus-infected group; $P < 0.01$.

Data of Table 11 showed that PBLG significantly increases activity of lymphoblastoid transformation. T/C is 156%.

EXAMPLE 18

The Effect of PBLG on Peritoneal Macrophage of Mice

The methods of animals are similar to previous section.

Macrophage culture. The macrophages were harvested 3 days after intraperitoneal injection of 2.5 ml thioglycollate into mice and isolated. Peritoneal lavage performed by using 8 ml of HBSS containing 10 U/ml heparin. When erythrocytes were visible, the cell pellet was treated with 0.2% NaCl for 30 seconds. Cells were then distributed in DMEM, which was supplemented with 10% (v/v) FCS, in either 96-well tissue culture plates ($2\times10^5$ cells/well) or 100-mm diameter plastic Petri dishes ($1\times10^7$ cells/dish), incubated for 3 h at 37° C. in an atmosphere of 5% $CO_2$. Non-adherent cells were removed by suction, and then freshly prepared complete media were added with the indicated experimental reagents.

Macrophage cytotoxicity assay. Killing of $^{51}$Cr-labelled K562 leukemia cells was measured using an 18-h $^{51}$Cr release assay. K562 target cells were labeled for 1 h at 37° C. with 500 μCi of $^{51}$Cr/$5\times10^6$ cells, washed by centrifugation, allowed to 'leak' for 1 h at 37° C. in complete DMEM containing 10% FCS, and washed again just before addition to macrophage cultures. Non-adherent cells were removed by washing three times after plating and the adherent macrophages were cultured for 24 h with a medium alone or with medium containing the indicated stimule.

Quadruplicate wells were used for each culture condition. The media were then removed, the cells were washed twice, and 450 μl of fresh medium were added to each well. The $^{51}$Cr—labeled K562 cells ($2\times10^5$) were then added to each well in a volume of 50 μl. After 18 h at 37° C. 100 μl of supernatants were removed and assayed for radioactivity in a gamma-spectrophotometer. Results are expressed as percentage specific $^{51}$Cr release (percentage cytotoxicity) as calculated by the following formula: % specific cytotoxicity=100×(experimental c.p.m.−spontaneous c.p.m.)/(total c.p.m.−spontaneous c.p.m.). Total c.p.m. was obtained from lysis of 50 μl $^{51}$Cr-labelled K562 cells ($2\times10^5$) with 200 μl of 0.5% sodium dodecyl sulphate. Spontaneous release was determined from $^{51}$Cr-labelled K562 cells incubated with medium alone. Spontaneous release was typically 30–35% of total c.p.m.

The data of experiments are summarized in Table 12.

TABLE 12

The effect of PGLB on macrophage (1)

| Treatment | n* | C.P.M. |
|---|---|---|
| Virus-infected | 10 | 601 ± 200 |
| PBLG + virus-infected | 10 | 1870 ± 259** |

*Number of samples.
**Significant different from virus-infected group; $P < 0.01$.

Staining Method

Added 0.02 ml of 5% washed chick red blood cell suspension to 0.5 ml of the peritoneal exudates, shook gently to mix and incubated at 37° C. for 5 min. Dipped two cover slips, closed to each other, and incubate for 30 min for the migration of the macrophages along the cover slips. Fixed and stained with Sharma stain. Examine microscopically for:

a. Phagocytic rate—number of macrophages with phagocytized chick red blood cells per 100 macrophages counted.

b. Phagocytic index—average number of phagocytized chick red blood cells of 100 macrophages counted.

TABLE 13

The effect of PBLG on macrophage (2)

| Treatment | n* | Phagocytic rate | Phagocytic index |
|---|---|---|---|
| Virus-infected | 20 | 11.50 ± 3.01 | 0.1 ± 0.02 |
| PBLG + virus infected | 20 | 45.50 ± 5.80** | 0.8 ± 0.07 |

*Number of samples.
**Significant different from virus-infected group; $P < 0.01$.

Data of Table 12–13 showed that PBLG significantly increases macrophage activity in virus-infected systems. It is 311% (T/C) for $^{51}$C method and 391% (T/C) for staining method. Phagocytic index increases to 800% (T/C).

EXAMPLE 19

The Effect of PBLG on Complement

Complement is a group of normal serum proteins. When the body invades by pathogenic microorganisms, the complement acting together with specific antibodies, exhibits its defensive function. It plays an important role in the anti virus-infectious immunity of the body.

The methods of animals are similar to previous section.
1. Materials
   a. Veronal buffer stock:
      NaCl 85.00 g, Barbituric acid 5.75 g, sodium barbital 3.75 g. Added 1500 ml of distilled water and heated to dissolve, added distilled water to 2000 ml.
   b. 0.1M EDTA—$Na_3$ stock:
      EDTA—$Na_3$ 37.23, NaOH 4.00 g
      Added the EDTA—$Na_3$ to 500 ml of distilled water and the NaOH to 100 ml of distilled water. Added it later to the former and EDTA—Na₃ would dissolve instantly. Adjusted pH to 7.5 with 1N NaOH and added distilled water to 100 ml.

c. 2% gelatin:

Gelatin 2.0 g added to distilled water 100 ml and heated to dissolve and stored at 4° C.

d. Gelatin veronal buffer (GVB)

| | |
|---|---|
| Veronal buffer stock | 100 ml |
| 0.03 M CaCl$_2$ | 10 ml |
| 0.01 M MgCl$_2$ | 10 ml |
| 2% gelatin | 100 ml |
| Added distilled water to | 1000 ml | e. Alsever solution:

Glucose 20.5 g, NaCl 4.2 g, sodium citrate 8.0 g

Dissolved in approximately 800 ml of distilled water and adjusted pH to 6.1 with citric acid. Added distilled water to 1000 ml. Sterilized by autoclaving.

f 0.01M EDTA—GVB:

Veronal buffer stock 360 ml, 0.1M EDTA—Na₃ stock 200 ml, 2% gelatin 100 ml, added distilled water to 2000 ml.

g. SRBS:

Mixed fresh sterile sheep blood with equal volume of Alsever solution and stored at 4° C. It could be used for several weeks.

h. Hemolysin:

(1) Preparatin of SRBC stroma:

Spun down the SRBC in 1 liter of sheep blood-alsever solution and washed several times with normal saline. Added 10l of distilled water which contained 4 ml of glacial acetic acid. Suspended the RBC and put in a 4° C. refrigerator overnight. Discarded the supernatant and packed the settled stroma at 2000 rpm. Suspended the stroma in 0.01M acetic acid, pH 5.0 and washed 5 times with the acetic acid solution. The acetic acid was then removed and the pH brought to neutral by wash the stroma 3 times each with 0.1M Na₂HPO₄ and normal saline. Packed the stroma by spinning at 7500 rpm. The packed SRBC stroma was then suspended in 300–400 ml of normal saline. Heated to 100° C. for 1 hour. Adjusted with sterile normal saline to 1 mg/ml. Added 0.01% merthiolate and stored at 4° C.

(2) Immunization of rabbits:

Immunized the rabbits by intravenous injections of the SRBC stroma in 2 weeks. Bled the animals 4 days after the last injection. Separated the serum. Inactivated at 56° C. for 30 min and stored at −20° C.

(3) Titration for optimal concentration of hemolysin:

By using 50% hemolysis (C'H$_{50}$) as end-point, SRBC sensitized by various concentrations of hemolysin were titrated against various amounts of guinea pig complement. Optimal concentration of hemolysin was determined by OD$_{541}$ reading which gave C'H$_{50}$ and standard curve plotted.

2. Methods:

a. Preparation of SRBC suspension—washed SRBC for 5 times with GVB to free from platelets. Filtered to remove cell aggregates. Adjusted the SRBC suspension to $1\times10^9$ RBC/ml.

b. Preparation of sensitized SRBC—warmed up 1 volume of hemolysin at the optimal concentration in a 37° C. water bath for 10 min and added equal volume of SRBC suspension at $1\times10^9$ cells/ml with stirring. Put in a water bath at 37° C. with shaking for 30 min. Then brought the temperature down in an ice-cool water bath with shaking. Washed the cold SRBC once with 0.01M EDTA—GVB, twice with GVB and prepared sensitized SRBC suspension at $5\times10^8$ cells/ml with GVB.

c. Determination of CH$_{50}$ unit and plotting of standard curves for the serum samples.

The data are summarized in Table 14.

TABLE 14

The effect of PBLG on complement

| Treatment | n* | C.P.M. |
|---|---|---|
| Virus-infected | 10 | 247 ± 10 |
| PBLG + virus-infected | 10 | 450 ± 50** |

*Number of samples.
**Significant different from virus-infected group; P < 0.01.

Table 14 showed that CPM of T/C is 182%. It means PBLG increases complement activity.

EXAMPLE 20

Effect of PBLG on Interleukin (IL-2 Activity)

IL 2 bioassay. Biologic activity of IL-2 was measured as described previously. Cells were seeded into 96-well, flat-bottomed microtiter plates at a concentration of $5\times10^4$ cells/well in 100 μl of growth medium without IL 2. Eighteen hours later, an equal volume of PBLG (100 μg/ml) or control medium was added and the cultures were incubated and additional 24 h. The cells were then labeled with 50 μl of [³H]thymidine at 20 μCi/ml (specific activity 6.7 Ci/mmol; New England Nuclear, Boston, Mass.) for 6 h. The cells in each well were then resuspended, harvested, and processed according to a filter pad technique. The acid-precipitable counts per minute per $2\times10^4$ cells were used. Radioactivity incorporated into the cells was measured. The data are summarized in Table 15.

TABLE 15

Effect of PBLB on IL-2 activity

| Treatment | ³H-TdR uptake* (1 × 10³ CMP) |
|---|---|
| Normal/A (non-treated) | 20.5 ± 2.2 |
| Normal/B (PBLG-treated only) | 22.0 ± 2.7 |
| Virus infected | 12.8 ± 12.0 |
| Virus infected and PBLG-treated | 21.8 ± 2.5** |

*IL-2 activity was measured after 6 h ³H-TdR incorporation
**Significant different from virus-infected group. P < 0.01

In this study, we have investigated the effect of PBLG on production of interleukins, which are known to be the mediators in immune system. The results indicated that PBLG increases IL-2 production. The increase of IL-2 by PBLG may contribute to the immunomodulatory effects, especially the recovery of immune function reduces by viruses infection.

In recent years more researches of antivirus drug has been placed on the rational approach to antiviral chemotherapy in which efforts are directed primarily toward the design and development of chemical compound that act selectively to inhibit virus replication without producing any adverse or cytoxic effects in the host cells, unfortunately, it is not successful. But PBLG showed some successful in this area.

Table 1–8 showed antiviral effect of PBLG. Tables 9–15 showed PBLG significantly increases host immune function. Increasing host's immune function is a best way for control of viral diseases. In fact, new and safe antiviral agent needs to have two functions: biologic antiviral effect and increasing immune function. Influenza virus infection and replication in the respiratory tract directly injures the nasal and tracheobronchial epithelium. Virus caused cellular apoptosis and loss of respiratory epithelial cells is one major reason for several of the symptoms that accompany infection of influenza virus, such as cough, depressed tracheobronchial clearance and disorder pulmonary function. Infection also caused host immune defenses and inflammation. For response of the infection and protection against reinfection, host needs development local and systemic cymptoms. Therefore, it is very important that antiviral drug can increase immune function while drug inhibits virus.

Infection of influenza virus is depended both on host factors, particularly the immune function. Natural killer cells (NK), for example, have an important role in limiting early speed of virus. As data of Table 11 shown that PBLG increased NK cell activity. PBLG increased NK activity at 175% and 158% for 50:1 and 100:1 of RBL-5, also 130% and 157% for 50:1 and 100:1 for YAC-1, respectively.

The thymus-dependent (T-cell) has an important role in resistance to influenza virus infection. Neither humans nor animals with depressed T-cell function appear unusually susceptible to influenza virus. Previous studies have shown that in virus infections transfer of sensitized T lymphocutes is more effective in transferring resistance than transfer of antibody. T lymphocytes may produce a variety of lymphokines, including interferon and various macrophage activating factors. Chemotactic lymphokines attract activated macrophages, which then also help in viral clearance. The most important role for T lymhocytes in viral infections is as cytotoxic effector cells. Human primed cytotoxic T-cell (CTL) can inhibit influenza virus. Table 13 indicated that PBLG could significantly increase activity of T-lymphocytes, including increase lymphoblastoid transformation. Above data indicated that PBLG could increase lymphoblastoid transformation at 156% (treatment/control).

The ability of macrophages to regulate immune reactions has been widely described. A lot of evidences indicated that a major role for macrophage during initiation and regulation of immune function. Macrophage has an important role in early stage of infection of viruses. Once initial implantation and infection occur, the next barrier a virus must overcome is the macrophage or other phagocytic cells. Course of subsequent infection depends on the results of the initial virus macrophage encounter. Adult macrophages are able to ingest and destroy virus. Also, Macrophages serve as ubiquitous cell that phagocytize and destroy viruses. Macrophages also serve later in the host response as effector cells.

As data of Table 12–13 indicated that PBLG could increase activity of macrophages. PBLG increases macrophage activity 311% (T/C) by $^{51}Cr$ method and 396% (T/C) by staining method. Therefore, it is a possible mechanism of inhibition virus by PBLG.

Table 14 showed that PBLG increased complement at 182% (T/C). Table 15 showed that PBLG increases IL-2 activity at 170% (T/C). Interleukin and complement play an important action for killing or destroying viruses in host.

Additional, it is known that polysaccharides might play an important role in increasing immune function. Some articles reported that it has increasing immune and antitumor effects.

The virus-host interactions are very complexities. Our goal of development of effective antiviral therapy should exploit these interactions to maximize increase host immune function and inhibit virus, meanwhile, this antiviral therapy is safe for human being. Many antiviral agents may actually inhibit host immune function. In fact, the major antiviral drugs can inhibit viral replication but also inhibit some host cell function and possess serious toxicity. For example, amantadine, idoxuridine, cytarabine, vidarabine are major antiviral drugs using in clinic now. Amantadine can inhibit myxoviurses. The most marked toxic effects of amantadine are insomnia, slurred speech, dizziness, ataxia and other central nervous system sign. Idoxuridine can inhibit the replication of herpes simplex virus in the cornea, however DNA synthesis of host cells is also inhibited. Cytarabine can inhibit DNA synthesis and interferes with replication of DNA viruses. But cytarabine also inhibits immune function in human. Vidarabine can inhibit herpes virus, but it is also produce more marked adverse gastrointestinal or neurologic side effects. Cytosine arabinoside (CA) also used for antiviral agent, but decreasing immune function of CA outweighed its antiviral activity. As mentioned above, so far there obviously still lacks any effective antiviral drug and at same time there is nothing to do with the side effect. Therefore, it is important that the development of virus therapeutic agents should allow the host increasing immune function. According to data of Table 1 to 8, PBLG can significantly inhibit influenza virus. According to data of Table 9 to 15, PBLG can significantly increase host immune function. PBLG is a new, select and safe drug of treatment influenza virus with significant antiviral effect, and it increases immune function of host. Therefore, PBLG is an excellent candidate for treatment of influenza virus infection in human.

As mentioned above, PBLG is a pure ingredient, which contained BLG's polysaccharide and Isatin B. PBLG can be used as a drug. BLG is a crude ingredient, which contained extracts of isatis tinctoria L or I indigotica Fort. BLG can be used as a drug and health food including tea forms. The pharmacological functions are similar between PBLG and BLG. But BLG is more sage than PBLG. In general, crude ingredient is always more safe than pure ingredient in botanical drugs.

EXAMPLE 20

Acute Toxicity

A. Route of Administration: the Oral Route

Oral $LD_{50}$ was determined to be high than 6.5 g/kg. Surviving mice showed no change in behavior the following days.

B. Route of Administration: Intravenous and Intraperiotoneal Injection (1) $LD_{50}$ of intraperitoneal injection of the PBLG in mice is 1205 mg/kg, and (2) $LD_{50}$ of interavenous injection of PBLG in mice is 610 mg/kg.

EXAMPLE 21

The Subacute Toxicity

The subacute toxicity of PBLG determined by rats after daily oral administration of 0.1% agar and PBLG over a period of 30 days, baby weight and consumption of food and water were evaluated every day. The subacute toxicity established that by comparison with the control group.

Those treated with 100 mg/kg of PBLG did not show any differences in consumption of water, food and body weights. Furthermore the animals had no depressive, excitatory or sleepiness symptoms. Microscopic inspection indicated no alteration in the stomach, liver, spleen and kidneys and in their relative weights (see table 16).

TABLE 16

The subacute toxicity of PBLG

| Group | Doses (mg/kg) | Weight (g) and relative weights | | | | | | |
|---|---|---|---|---|---|---|---|---|
| | | Body (B) | Liver (L) | L/B | Spleen (S) | S/B | Kidneys (K) | K/B |
| Agar 1% | — | 170.5 ± 10.1 | 5.286 ± 0.4 | 0.031 | 0.852 ± 0.08 | 0.005 | 1.093 ± 0.090 | 0.007 |
| PBLG | 10 mg/kg | 169.0 ± 15.9 | 5.70 ± 0.600 | 0.034 | 0.840 ± 0.61 | 0.0050 | 1.0175 ± 0.09 | 0.0059 |
| PBLG | 50 mg/kg | 170.8 ± 16.0 | 5.20 ± 0.620 | 0.030 | 0.793 ± 0.70 | 0.0046 | 1.100 ± 0.10 | 0.0064 |
| PBLG | 100 mg/kg | 168.9 ± 15.8 | 5.10 ± 0.580 | 0.030 | 0.805 ± 0.79 | 0.0048 | 0.980 ± 0.08 | 0.0058 |

Each value represents the mean±SE obtained from 20 rats. The PBLG was administered orally during 3-consecutive days.

Additional, after daily administered by intragastric route of 200 mg/kg during 30 consecutive days, the behavior of the animal remained normal, and no abnormalities were found in the liver and kidney function, and histological picture of important organs. The $LD_{50}$ in mice of oral is 6.5 g/kg, which is more 100 times higher than the dose used in clinical trials for human being. It is obviously to determine the very low toxicity of PBLG.

The World Health Organization (WHO) established the classification of chemicals in 1973, according to relative toxicity. A chemical, which has oral $LD_{50}$ of administration in mice>5 g/kg, is very low toxic. Therefore, PBLG is a safe drug. This low toxicity was confirmed by sub-acute tests and absence of macroscopic lesions of the organ examined.

The preparation of PBLG is simple and can be accomplished by the extraction methods set forth above or any conventional methods for extracting the active ingredients from the plant tissues. The novelty of the present invention resides in the mixture of the active ingredients in the specified proportions to produce PBLG and in the preparation of dosage units in pharmaceutically acceptable dosage form. The term "pharmaceutically acceptable dosage form" as used hereinabove includes any suitable vehicle for the administration of medications known in the pharmaceutical art, including, by way of examples, tablets, capsules, syrups, elixirs, and solutions with specified ranges of PBLG concentration. The present invention provides novel methods for inhibiting viruses and increasing immuno-function with easily produced, safe pharmaceutical agent.

It will thus be shown that there are provided compositions and methods which achieve the various objects of the invention, and which are well adapted to meet the conditions of practical use. As various possible embodiments might be made of the above invention, and as various changes might be made in the embodiments set forth above, it is to be understood that all matters herein described are to be interpreted as illustrative and not in a limiting sense.

What is claimed as new and desired to be protected by letters patent is set forth in the appended claims:

1. A safe botanical composition for treatment of influenza and increasing immune function comprising 30~70% by weight of Polysacchatide of *Isatis tinctora* L, *Isatis indigotica* Fort or *Baphica cusia* Bremek and 30~70% by weight of Isatin B.

2. A process for producing polysaccharides from *Isatis tinctora* L., *Isatis indigotica* Fort or *Baphica cusia* Bremek comprising:

a) extracting the dried powder of the plant with hot water;
b) filtering the extract;
c) dialyzing the filtrate against running water though cellulose;
d) concentrating the filtrate;
e) adding ethanol to the concentrated filtrate to obtain a first precipitate;
f) extracting said first precipitate with aqueous 0.4% sodium borate;
g) collecting the residue of said extraction by centrifugation and dissolving the residue in water;
h) acidifying the solution with acetic acid, dialyzing the solution against running water, and lyophilizing the solution to produce a first fraction;
i) adding ethanol to the first fraction and collecting a second precipitate by centrifugation;
j) dissolving said second precipitate in water and chromatographing said solution in a column of sepharose;
k) eluting said column with water to produce a second and third fraction;
l) adding ethanol to said second and third fractions to produce a third precipitate and collecting said third precipitate by centrifugation;
m) drying said third precipitate by washing it with acetone followed by ether and further drying said third precipitate in a vacuum to produce the polysaccharides.

3. A process for producing Isatin B comprising:

a) extracting the dried powder of a plant containing Isatin B with hot water;
b) filtering the extract;
c) dialyzing said filtrate against running water through cellulose;
d) concentrating said filtrate;
e) adding ethanol to said concentrated filtrate to obtain a first precipitate;
f) extracting said first precipitate with aqueous 0.4% sodium borate;
g) collecting the residue of said extraction by centrifugation and dissolving said residue in water;
h) acidifying said solution with acetic acid, dialyzing said solution against running water and lyophilizing said solution to obtain a first fraction;
i) adding ethanol to said first fraction to obtain a second precipitate and collecting said second precipitate by centrifugation;
j) dissolving said second precipitate in water and chromatographing said solution in a column of sepharose;

k) eluting said column with water to obtain a second and third fraction;

l) precipitating said second and third fraction with ethanol to obtain a third precipitate and collecting said third precipitate by centrifugation;

m) drying said third precipitate by washing with acetone followed by ether and further drying said third precipitate by vacuum to produce Isatin B.

4. A process for producing Isatin B comprising:

a) extracting the dried powder of a plant containing Isatin B with hot water;

b) filtering the extract;

c) extracting said filtrate with methanol;

d) obtaining a residue by recovering said methanol under reduced pressure;

e) extracting said residue with chloroform;

f) chromatographing said extract on silica gel using chloroform as the eluent;

g) concentrating said eluate and rechromatographing said eluate on silica gel G using chloroform as the eluent;

h) crystallizing lsatin B from said chloroform;

i) recrystalizing Isatin B and drying Isatin B under vacuum.

5. A safe botanical composition for treatment of influenze and immune fraction comprising:

a) polysaccharides from *Isatis tinctora* L., *Isatis indigotica* Fort or *Baphica cusia* Bremek wherein said polysaccharides are determined by electrophoresis and the spot was detected with the naphthol-sulfuric acid reagent;

b) Isatin B wherein said Isatin B is determined by high pressure liquid chromatography.

6. A botanical composition for treatment of influenza and increasing immune function of claim 2 wherein said composition is very safe and oral $LD_{50}$ is >5.0 g/kg.

* * * * *